US006896914B2

(12) United States Patent
Chapnick et al.

(10) Patent No.: US 6,896,914 B2
(45) Date of Patent: May 24, 2005

(54) METHOD FOR NORMALIZING INSULIN LEVELS

(76) Inventors: David I. Chapnick, 9282 Broad St., Boca Raton, FL (US) 33434; Linda G. Chapnick, 9282 Broad St., Boca Raton, FL (US) 33434

( * ) Notice: Subject to any disclaimer, the term of this patent is extended or adjusted under 35 U.S.C. 154(b) by 0 days.

(21) Appl. No.: 10/280,332

(22) Filed: Oct. 25, 2002

(65) Prior Publication Data

US 2003/0092669 A1 May 15, 2003

Related U.S. Application Data

(60) Provisional application No. 60/343,576, filed on Oct. 26, 2001.

(51) Int. Cl.[7] ........................ A61K 35/78; A61K 31/715
(52) U.S. Cl. ........................ 424/769; 424/725; 424/777; 514/54
(58) Field of Search ................................ 424/725, 769, 424/777; 514/44

(56) References Cited

U.S. PATENT DOCUMENTS

| 4,372,948 A | 2/1983 | Yoshikumi et al. |
| 5,344,824 A | 9/1994 | Ohkuma et al. |
| 6,319,510 B1 * | 11/2001 | Yates |
| 2002/0035071 A1 * | 3/2002 | Pitha et al. |

OTHER PUBLICATIONS

Raonimalala et al. Annales de la Nutrition et de l'Alimentation. 1980. vol. 34 (4), pp. 735–744, CAPLUS abstract enclosed.*
W. Langhans, & E. Scharrer, Changes in Food Intake and Meal Patterns Following Injection of D–Mannoheptulose in Rats, Behavioral and Neural Biology 38, pp. 269–286, (1983).
W. Nelkin, Diabetogenicity of Ketoheptoses, II, Relative Potencies, Acta Physiologica Academiae Scientarium Hungaricae, Tomus 41 (2), pp. 175–177, (1972).
W. Nelkin, Diabetogenicity of Ketoheptoses, III,Modification of Structure, Acta Physiologica Acadamiae Scientarium Hungaricae, Tomus 41, pp. 179–181, (1972).
Josef K. Viktora, et al., Effect of Ingested Mannoheptulose in Animals and Man, Metabolism 18, No. 2, pp. 87–102, (1969).
Brian F. Johnson & Frederick W. Wolf, Trial of Mannoheptulose in Man, Metabolism 19, No. 5, pp. 354–362, (1970).
A. Lev–Ran, et al., Effect of Intravenous Infusion of D–Mannoheptulose on Blood Glucose, Journal of Endocrinolgoy 47, pp. 137–138, (1970).
Annonymous, Nutrition Reviews 27, No. 7, pp. 206–208, (1969).
E. P. Paulsen, Mannoheptulose and Insulin Inhibition, Annuals New York Academy of Science 150, pp. 455–456, (1968).

Milan Rezek, et al., Insulin Dependence of Paradoxial Overeating: Effect on Mannoheptulose, Somatostatin, and Cycloheximide, American Journal of Physiol 236 (3), pp. E205–E211, (1979).
Saul Genuth & Harold E. Lebovitz, Stimulation of Insulin Release by Corticotropin, Endocrinology 76, No. 6, pp. 1093–1099, (1965).
F. B. La Forge, D–Mannoketoheptose, A New Sugar From the Avocado, The Journal of Biological Chemistry 28, pp. 511–527, (1916–1917).
Thomas Laedtke, et al., Overnight Inhibition of Insulin Secretion Restores Pulsatility and Proinsulin/Insulin Ratio in Type 2 Diabetes, American Journal Physiol Endocrinol Metab. 279, pp. E520–E528, (2000).
Saul M. Genuth, M.D., Plasma Insulin and Glucose Profiles in Normal, Obese, and Diabetic Persons, Annals of Internal Medicine 79, pp. 812–822, (1973).
Paul B. Beeson, M.D.and Walsh McDermott, M.D., Textbook of Medicine 14th Edition, pp. 1375–1386, (1975).
Edna M. Montgomery and C. S. Hudson, The Synthesis of D–Mannoheptulose, and the Preparation of Some of its Derivatives, The Journal of the American Chemical Society 61, pp. 1654–1658, (1939).
Nelson K. Richtmyer, D–Manno–Heptulose, Isolation Form the Avocado, Methods in Carbohydrate Chemistry 1,pp. 173–176, (1962).
Timothy M. Chan and J. P. Dehaye, Hormone Regulation of Glucose Metabolism in the Genetically Obese–Diabetic Mouse (db/db), Diabetes 30, pp. 211–218 (1981).
K. Hermansen, Pancreatic D–Cell Recognition of D–Glucose, Diabetes 30, pp. 203–210, (1981).
E. Simon, Ph.D. and P. F. Kraicer, Ph.D., The Blockade of Insulin Secretion by Mannoheptulose, Israel Journal of Medical Science 2, No. 6, pp. 785–799, (1966).
B. Johnson, et al., The Efficacy of Oral Mannoheptulose in Monkey and Man, Diabetes 18, Suppl. 1, p. 360, (1969).
U.S. patent application Ser. No. 09/950,052, Pitha et al., filed Mar. 21, 2002.
Raonimalala, A.F., et al., Action Des Glucides Solubles Du Fruit De L'Avocatier (Persea Gratissima Gaertner) Sur L'Utilisation Du Calium Chez Le Rat, Annales De La Nutrition Et De L'Alimentation (1980), 735–44, 34(4).

* cited by examiner

Primary Examiner—Christopher R. Tate
(74) Attorney, Agent, or Firm—Bernard Rhee; Powell, Goldstein, Frazer & Murphy LLP

(57) ABSTRACT

The invention is directed to a dietary supplement which contains mannoheptulose. Mannoheptulose occurs naturally in avocado fruit. The dietary supplement and its method of use can lower serum insulin levels and lower a subject's weight. The dietary supplement in its disclosed form includes a controlled release system for mannoheptulose. The dietary supplement may also include one or more amino acids.

7 Claims, No Drawings

METHOD FOR NORMALIZING INSULIN LEVELS

This application claims the benefit of Provisional Application No. 60/343,576, filed Oct. 26, 2001.

BACKGROUND OF THE INVENTION

The present invention generally relates to an oral dietary supplement which decreases serum insulin levels. High levels of serum insulin (i.e., hyperinsulinemia) is a major health problem. Hyperinsulinemia promotes hypertension, suppresses the release of growth hormone, and can harm the kidneys. The vascular system can be severely damaged by prolonged exposure to high insulin levels. Excess insulin can also increase the risk and progression of certain cancers and is a contributory factor in benign prostate enlargement.

High serum insulin is associated with the development of obesity and a large number of related health problems including degenerative joint disease, atherosclerosis, and impotence. Specifically, obesity has been associated with excess insulin production and reduced insulin sensitivity which are both risk factors for Type II diabetes. Therefore, obese individuals face a significant risk for developing Type II diabetes. It is possible to mitigate or control either Type II diabetes or obesity by effectively controlling the other.

There has been an increasing incidence of obesity in our society and an absence of effective weight control. The role of hyperinsulinemia in the origin and maintenance of idiopathic obesity is well established. It is widely known in the medical community that an increase in fasting insulin is the critical difference between thin and obese persons. Specifically, fat cannot be released from storage as long as insulin is present in the blood. This may be why dieting alone, i.e. caloric restriction, has not been effective in controlling obesity. When insulin is circulating in the blood stream, the body will not release significant fat stores, even when a person exercises and restricts their food intake. Such circumstances would only result in the loss of lean body mass and fluid.

In normal healthy individuals, insulin blood levels fall to zero when the serum glucose level drops below approximately 83 mg %. In obese individuals, insulin blood levels rarely fall to zero. As little as one microunit of insulin in serum will prevent the breakdown of stored fat. Even starvation does not bring insulin levels to normal in obese subjects.

As people age, sensitivity of cells to insulin generally decreases due to sedentary lifestyles, poor diet, and the natural aging process. The pancreatic response to this is often hyper-secretion of insulin. Therefore, it is difficult for people to lose a significant amount of body fat as long as they suffer from insulin overload. A noticeable effect of excess serum insulin is constant hunger. This results in a vicious cycle where overeating causes more body fat to accumulate and in turn, causes greater amounts of insulin secretion. The most immediate and noticeable effect of too much insulin may be unwanted weight gain.

Mannoheptulose is a seven carbon sugar which is naturally found in avocado fruit. Mannoheptulose inhibits hexokinase in a predominantly competitive manner. Hexokinase is an enzyme which catalyzes the phosporylation glucose to glucose -6-phosphate (G6P), which is the first reaction of glycolysis. Therefore, ingestion of mannoheptulose is a logical method of decreasing insulin serum levels.

Previously, the potential usefulness of this seven-carbon ketogenated sugar has been limited by its unpleasant side effects (e.g., diarrhea, nausea) and poor absorption on oral administration. There are problems with unpleasant side-effects, and problems of transient hypoglycemia. Scientists have believed that orally administered mannoheptulose was limited to the extent which it could be absorbed in man, because of its laxative effect when orally administered. This effect is most likely an osmotic effect, similar to that of mannitol. Mannoheptulose has been shown to lower fasting and glucose stimulated peak insulin release in mammals including man.

The only oral pharmaceutical preparation available for hyperinsulinemia is diazoxide (sold under the tradename Proglycem®). which is also sold as an intravenous anti-hypertensive (sold under the tradename Hyperstat®). However, its usefulness has been limited by its significant side-effects and serious drug interactions. Treatment of obese patients with diazoxide lowers insulin levels, but also drops blood pressure dangerously and can intensify the effects of anticoagulants. The diazoxide intravenous solution must be administered with great care so as to not inject it subcutaneously, intramuscularly or into body cavities. Extravasation must be avoided because the solution is alkaline and very irritating.

Many features, advantages, and objects of the present invention will become apparent to one with skill in the art upon examination of the detailed description. It is intended that all such features, advantages, and objects be included herein within the scope of the present invention.

SUMMARY OF THE PRESENT INVENTION

One embodiment of the present invention is an oral dosage form which includes mannoheptulose and a controlled release system. It may optionally include one or more amino acids.

Another embodiment of the present invention is a method for lowering serum insulin levels using the oral dosage form. An alternate embodiment of the present invention is a method for weight loss using the oral dosage form. In yet another embodiment of the present invention, the invention is a method of preparing the oral dosage form.

DETAILED DESCRIPTION OF THE PRESENT INVENTION

The present invention provides a novel oral dosage form and method which have many uses. Possible uses include, but are not limited to, reducing a subject's serum insulin levels and controlling obesity or otherwise affecting a subject's weight. The subject may be any animal in which one desires to affect a biological response or elicit therapeutic result. It is preferred that the subject be a mammal. It is most preferred that the subject be human.

The dosage form includes mannoheptulose, a seven carbon sugar which naturally occurs in avocado fruit. It most preferably includes the dextro (i.e., right or d-) isomer of mannoheptulose. The dosage form of the present invention can include any amount of mannoheptulose which will affect a biological response or elicit a therapeutic result from the subject. For example, the biological response or therapeutic result may be to reduce fasting insulin or control a subject's weight. The range of the amount of mannoheptulose in the oral dosage form of the present invention can be from approximately 1 mg–5 gm. The preferred range is approximately 10 mg–1000 mg. The most preferred range is approximately 50 mg–250 mg.

The dosage form of the present invention can be any dosage form that can be administered orally and elicit a desired response or result from a subject. Examples of dosage forms of the present invention include, but are not limited to tablets, capsules, semisolids, liquids, solutions, suspensions, and emulsions. Tablets and capsules are preferred dosage forms. The most preferred dosage form is a tablet.

The dosage form of the present invention includes a controlled release system. The controlled release system may be any system which can affect the dissolution or bioavailability of mannoheptulose. Possible systems include, but are not limited to slow release systems, extended release systems, delayed release systems, multilayer tablets, semipermeable membranes, gelatin capsules, and the use of semisolids. Controlled release may possibly be achieved by changing diffusion, dissolution, ion-exchange, or osmotic pressure. Controlled release may also be achieved by the use of various excipients such as binding agents, moistening agents, surfactants, disintegrants, lubricants, diluents, glidants, and adsorbents. The controlled release may also be achieved by adjusting formulation factors such as effective surface area of the drug, compression, granule size, and coatings. A preferred controlled release system of the present invention is an enteric coating. The most preferred controlled release system of the present invention is one which uses of carboxymethylcellulose.

The oral dosage form of the present invention may optionally include one or more amino acids. The amino acids provide a source of energy for a subject, and because they are not sugars, they do not affect insulin or glucose serum levels. Any amino acid which provides a source of energy for a subject may be used. A possible amino acid is 1-aspartic acid. The most preferred amino acid is 1-glutamic acid.

The present invention is also a method for using the oral dosage form of the present invention (i.e., the novel oral dosage form) to achieve a desired response, a desired therapeutic outcome or affect a desired therapeutic condition. One example of a method of the present invention is a method which uses the novel oral dosage form to decrease serum insulin levels. Another example of a method of the present invention is a method which uses the novel oral dosage form to decrease a subject's weight. Another example of a method of the present invention is a method which uses the novel oral dosage form to mitigate or control any condition secondary to or relating to high serum insulin levels. Yet another example of a method of the present invention is a method which uses the novel oral dosage form to deplete a subject's stored fat. The most preferred method of the present invention is a method which uses the novel oral dosage form to decrease a subjects weight.

The present invention is also a method for preparing the novel oral dosage form of the present invention. A preferred is a method of preparation includes the step of extracting mannoheptulose from avocado fruit by ethanolic extraction. The extraction may be directly or indirectly from avocado fruit. Many varieties of avocado can be used. It is preferred to use a variety of avocado which is inexpensive, easily attainable, and which has a high concentration of mannoheptulose. The most preferred varieties of avocados for use in the present invention are Booth 7 and Lula.

All stereoisomers of the compounds of the present invention are contemplated and within the scope of the invention, either in admixture or in pure or substantially pure form. The definition of mannoheptulose and amino acids according to the invention embraces all possible stereoisomers and their mixtures. It very particularly embraces the forms and the isolated optical isomers having the specified activity. The forms can be resolved by physical methods, such as, for example, fractional crystallization, separation or crystallization of diastereomeric derivatives or separation by chiral column chromatography. The individual optical isomers can be obtained from the racemates by any conventional methods.

The present invention is illustrated by the following examples that should not be considered limiting.

EXAMPLE 1

A. Methodology

The purpose of this study was to ascertain if excess levels of serum insulin could be safely reduced (i.e., without inducing hyperglycemia) in a group of overweight male human subjects using d-mannoheptulose (MH). A six-week double-blind study would also determine if combining an amino acid (i.e., 1-glutamic acid) and enteric coating would enhance the bioavailability and efficacy of oral d-mannoheptulose and prevent diarrhea. The amount of amino acid used was 500 mg per dose.

Thirteen healthy male human subjects, aged thirty-seven to fifty-seven, each at least forty pounds overweight, underwent screening blood testing. The Automated Chemistry Profile used included the following measurements: Serum Glucose, BUN, Creatinine, BUN/Creatinine Ratio, Uric Acid, Sodium, Potassium, Chloride, Carbon Dioxide, Calcium, Phosphorous, Total Protein, Albumin, Globulin, A/G Ratio, Total Bilirubin, Alkaline Phosphatase, LDH, AST, ALT, and Iron. A Lipid Profile, and CBC with Differential were also measured. Tests specific to this study included C-Peptide, Serum Insulin, and Hemoglobin A1c.

Subjects were randomly placed into two groups: "A" (Purple Caps) and "B" (Green Caps). Neither subject nor investigator knew which dosage forms were active and which were placebo. Once a week for three weeks, all subjects came to a local medical office while fasting and, stayed for a period of at least four hours. Blood was drawn from each subject in the fasting state, immediately following a high sugar meal, and at one and three hours after taking 500 mg. of MH. Additionally, fasting blood levels of glucose and insulin were drawn two times a week.

The intent was to cross over the patient test groups at the end of three weeks. But, the response of the group receiving active substance was so obvious that any attempt to continue the double-blind methodology in secrecy was pointless. The active compound group not only stabilized their eating patterns, but also experienced considerable weight loss.

At the end of the third week, the code was broken, confirming that the subjects with the dramatic response were getting the active oral dosage form. Thereafter, all subjects were given the same active dosage form.

Prior to receiving the active oral dosage form, every subject had demonstrated elevated C-Peptide levels and elevated glucose:insulin Ratio (0.41 times glucose mg/% minus 34 equals insulin in microunits).

B. Findings and Conclusion

Compared to the baseline obtained at the beginning of the study, average levels of fasting serum insulin were 26.41% lower at the end of study. Fasting serum glucose levels were an insignificant 1.52% higher at the end of the study, indicating that the significant suppression of fasting insulin in response to MH did not induce an increase in serum glucose or the development of hyperglycemia.

In response to a same-day glucose challenge, serum glucose and insulin levels increased as expected. Three hours after administering one dose of MH, serum insulin levels were, on average, 22.4% lower than the baseline fasting insulin levels obtained just four hours earlier. Average glucose levels increased an insignificant 1.92%. This same-day test of study subjects demonstrated that the immediate insulin suppressing effect of MH does not result in an increase in serum glucose or in the development of acute hyperglycemia.

The serum glucose averages excluded one study participant who was hypoglycemic when entering the study, but became normalglycemic in response to using the MH compound. This desirable therapeutic benefit may have occurred in response to the normalization of insulin metabolism induced by the MH.

End of study C-peptide levels were only obtained on two subjects. The results showed an average reduction of 43% in C-peptide levels at the end of the study compared to baseline, indicating a normalization of insulin metabolism.

All study participants reported significant weight-loss and reduction in carbohydrate craving. Since this study was designed to determine the hematological effects of administering MH to overweight human males, data on weight loss was not collected. There were no hematological or symptomatic indications of toxicity in any of the subjects. Patient compliance was high, due in part to the three-times-a-week visits to the local medical center.

Enterically coated MH proved to be effective short-term and long-term, in lowering elevated serum insulin. Moreover, not one instance of nausea or diarrhea was reported. The relatively small dose of MH can be expected to reliably lower insulin levels without inducing hyperglycemia. The combination of predictable insulin control and absence of adverse events supports using this preparation in for weight loss.

TABLE 1

Intake (FASTING) Blood Determinations

| Subject Number | Glucose (mg./%) | Insulin (uU) | C-Peptide (ng./mL) |
| --- | --- | --- | --- |
| 1-1 | 99 | 15.1 | 4.1 |
| 1-2 | 103 | 17.8 | 5.4 |
| 1-3 | 132* | 83.1* | 11.9 |
| 1-4 | 90 | 12.8 | 4.8 |
| 1-5 | 88 | 14.3 | 4.5 |
| 1-6 | 99 | 24.3 | 6.3 |
| 1-7 | 54* | 11.1 | 5.8 |
| 0-1 | 107 | 23.1 | 5.4 |
| 0-2 | 107 | 18.7 | 4.5 |
| 0-3 | 86 | 13.7 | 4.4 |
| 0-4 | 94 | 23.7 | 5.0 |
| 0-5 | 100 | 18.5 | 4.6 |
| 0-6 | 98 | 20.1 | 5.1 |

TABLE 2

High Peak (Glucose Challenge)

| Subject Number | Glucose (mg/%) | Insulin (uU) | C-Peptide (ng/mL) |
| --- | --- | --- | --- |
| 1-1 | 127 | 110.6 | 8.4 |
| 1-2 | 118 | 44.5 | 8.0 |
| 1-3 | 91 | 18.1 | 4.3 |
| 1-4 | 179 | 154.3 | 9.6 |
| 1-5 | 184 | 174.6 | — |
| 1-6 | 97 | 83.5 | — |
| 1-7 | 92 | 33.5 | 16.0 |
| 0-1 | 106 | 152.9 | 12.6 |
| 0-2 | 185 | 86.0 | — |
| 0-3 | 97 | 54.6 | — |
| 0-4 | 112 | — | — |
| 0-5 | 144 | 312 | 22.0 |
| 0-6 | 101 | 69.6 | — |

TABLE 3

One Hour Post-MH

| Subject Number | Glucose (mg/%) | Insulin (uU) | C-Peptide |
| --- | --- | --- | --- |
| 1-1 | 97 | 83.2 | — |
| 1-2 | 108 | 25.3 | — |
| 1-3 | — | — | — |
| 1-4 | 95 | 71.4 | — |
| 1-5 | 93 | 49.2 | — |
| 1-6 | 100 | 14.6 | — |
| 1-7 | 90 | 177.3 | — |
| 0-1 | 118 | 68.0 | — |
| 0-2 | 114 | 2.2 | — |
| 0-3 | 100 | 17.1 | — |
| 0-4 | Disc. | Disc. | Disc. |
| 0.5 | Disc. | Disc. | Disc. |
| 0-6 | Disc. | Disc. | Disc. |

TABLE 4

Three Hour Post MH

| Subject Number | Glucose (mg/%) | Insulin (uU) | C-Peptide |
| --- | --- | --- | --- |
| 1-1 | 104 | 14.5 | — |
| 1-2 | 106 | 17.9 | — |
| 1-4 | 94 | 15.5 | — |
| 1-5 | 84 | 10.5 | — |
| 1-6 | 92 | 14.3 | 7.9 |
| 1-7 | 88 | 12.3 | — |
| 0-1 | 123 | 12 | — |
| 0-2 | 111 | 4.0 | — |
| 0-3 | 80 | 16.1 | — |

TABLE 5

End Of Study Blood Levels

| Subject Number | Glucose (mg/%) | Insulin (uU) | C-Peptide |
| --- | --- | --- | --- |
| 1-1 | 95 | 8.4 | 2.2 |
| 1-2 | 106 | 17.9 | — |
| 1-5 | 96 | 8.2 | — |
| 1-6 | 90 | 12.6 | — |
| 1-7 | 94 | 7.8 | 3.4 |
| 0-1 | 98 | 20.1 | — |
| 0-2 | 127* | 17.3* | — |

*It should be noted that with regards to Table 4, patient samples 0–4 through 0–6 are missing. Also, with regards to Table 5, patient samples 0–3 through 0–6 are missing. These are due to patients dropping out of the study or laboratory errors such as lost specimens.

EXAMPLE 2

A. Methodology

All study subjects had serum insulin, blood glucose, and C-peptide levels drawn. The relationship of insulin to glucose was determined by the following formula:

Glucose (mg %)×0.41−34=Insulin

Thus:

83 mg % glucose×0.41=34.03−34=0.03 or, insulin vanishes from the blood at 83 mg %.

Subjects were male and females under the age of 50, who were at least 45 pounds overweight according to the body mass index (BMI). None were found to be hyperglycemic or to spill sugar in urine. All were found to have fasting insulin levels of at least 30, and all were found to be hyperinsulinemic with regards to the glucose:insulin ratio. Sixteen subjects were given 500 mg of d-manno-heptulose (MH) in enteric coated capsules. Sixteen subjects were given placebo in similar appearing capsules.

All subjects received doses four times a day, which were orally ingested in the presence of the investigator. Insulin and glucose levels were drawn one hour after ingesting capsules, two hours afterwards, and four hours afterwards. C-peptide levels were measured once a day. Patients were asked to keep meal logs, recording everything that they ingested by mouth, on a daily basis, for the duration of the study. The subjects and investigators were both blind to the group receiving active medication. At the end of three weeks, the test groups were switched. The group receiving active dosage forms was switched with the group receiving placebo.

The initial time period was designed to be three weeks. However, four patients dropped out because they found the schedule too demanding. Nine of the control group patients expressed a desire to quit, and four were allowed to withdraw. The remaining twenty-four subjects completed the six week period.

B. Findings & Conclusions

The twelve subjects designated A group were found to have been taking the active medication. All demonstrated similar changes in blood chemistry. Two hours after administration of the MH, insulin levels had decreased by an average of 81%. Fasting insulin was found to be 0 (zero) in all subjects after having taken active medication for three days. Control subjects (those ingesting placebo) showed no changes in glucose:insulin ratio, or in fasting insulin levels.

All twelve active medication subjects lost weight and experienced changes in food preference. Average weight loss was 1.6 lbs. per day per subject, with the greatest being 1.9 lbs. per day, and the lowest being 1.2 lbs. per day. Although the methodology for measurement of grams of carbohydrate consumed per day had not been provided, all MH recipients reported diminished tolerance for high-sugar foods while on medication.

When the original twelve active principle patients were switched to placebo, the insulin suppressing action continued to be seen for eleven days, on average. Weight loss continued for as long as patients were followed, although average loss decreased to 0.7 lbs. per day. At the conclusion of the twenty-one days of placebo ingestion, the original MH group was still reporting diminished desire for and tolerance of sugar.

Changing from placebo to MH, the control group showed a faster response to MH than did the original group. Fasting insulin had been restored to 0 (zero) by the middle of the second day of MH administration, after six doses had been taken. This was four doses faster than the original group. Weight loss also was greater, with average per day losses over the twenty-one days at 2.2 lbs.

We conclude that enterically coated d-mannoheptulose begins to effectively lower plasma insulin levels within two hours of administration. This effect is sustained by dosing every six hours and, three days of continuous ingestion affects changes in food preference that contribute to the drug's efficacy. Discontinuation of MH does not result in immediate reversion to baseline.

It should be emphasized that the foregoing description and examples have been presented for purpose of providing a clear understanding of the invention. The description is not intended to be exhaustive or to limit the invention to the precise examples disclosed. Obvious modifications or variations by one with skill in the art are possible in light of the above teachings without departing from the spirit and principles of the invention. All such modifications and variations are intended to be within the scope of the present invention.

What is claimed is:

1. A solid oral dosage form to be swallowed, wherein said oral dosage form comprises 50 mg–250 mg of mannoheptulose, carboxymethylcellulose, and 100 mg–500 mg of l-glutamic acid.

2. A method of decreasing serum innsulin, in a subject in need thereof, comprising said subject ingesting the dosage form of claim.

3. A method for controlling weight, in a subject in need thereof, comprising said subject ingesting the dosage form of claim.

4. A solid oral dosage form to be swallowed, wherein said oral dosage form comprises 10 mg–1000 mg of mannoheptulose, an enteric coating, and glutamic acid.

5. A solid oral dosage form to be swallowed, wherein said oral dosage form comprises 50 mg–250 mg of mannoheptulose, an enteric coating, and glutamic acid.

6. A method of decreasing serum insulin in a subject ingesting in need thereof comprising said subject a solid oral dosage form to be swallowed, wherein said oral dosage form comprises 10 mg–1000 mg of mannoheptalose, an enteric coating, and glutamic acid.

7. A method for controlling weight, in a subject in need thereof comprising said subject ingesting a solid oral dosage form to be swallowed, wherein said oral dosage form comprises 10 mg–1000 mg of mannoheptulose, an enteric coating, and glutamic acid.

* * * * *